United States Patent [19]

Lewis et al.

[11] Patent Number: 5,246,426
[45] Date of Patent: Sep. 21, 1993

[54] CATHETERIZATION SYSTEM

[75] Inventors: Jeffrey P. Lewis, Wyomissing; Robert A. Szurgot, Mt. Penn; Jeffrey M. Moyer, Harrisburg, all of Pa.

[73] Assignee: Arrow International Investment Corp., Wilmington, Del.

[21] Appl. No.: 899,785

[22] Filed: Jun. 17, 1992

[51] Int. Cl.$^5$ ............................................. A61M 5/178
[52] U.S. Cl. ..................................... 604/168; 604/164
[58] Field of Search ....................... 128/656, 657, 658; 604/168, 164, 52, 53, 170

[56] References Cited

U.S. PATENT DOCUMENTS

| | | | |
|---|---|---|---|
| 4,417,886 | 11/1983 | Frankhouser et al. | 604/53 |
| 4,525,157 | 6/1985 | Vaillancourt | 604/168 |
| 4,655,750 | 4/1987 | Vaillancourt | 604/168 |
| 4,772,264 | 9/1988 | Cragg | 604/168 |
| 4,863,431 | 9/1989 | Vaillancourt | 604/168 |
| 4,894,052 | 1/1990 | Crawford | 604/63 |
| 4,952,207 | 8/1990 | Leuieux | 604/168 |
| 4,961,729 | 10/1990 | Vaillancourt | 604/168 |
| 5,120,319 | 6/1992 | Van Heugten et al. | 604/168 |

FOREIGN PATENT DOCUMENTS 139091 5/1985 European Pat. Off. ............ 604/168

OTHER PUBLICATIONS

Arrow International, Inc. EID Catheter.

Primary Examiner—John G. Weiss
Attorney, Agent, or Firm—Amster, Rothstein & Ebenstein

[57] ABSTRACT

This invention relates to an improved arterial catheterization system which is designed to allow the user to quickly visualize the early flashback of blood after penetration of a vessel. The improved arterial catheterization system of this invention allows for minimum blood loss during initial penetration of the blood vessel. Specifically, this invention is directed to a system for introducing an over-the-needle catheter into a blood vessel, and comprises an inserter unit having a hollow needle and a catheter having a lumen such that the catheter is adapted to be carried on the needle. The catheter and needle cooperate to form a first flashback chamber therebetween. The first flashback chamber is at least partially translucent and allows for the visualization of blood flow upon insertion of the needle into a blood vessel. A guide wire, which is slidably mounted on the inserter unit within the needle, is dimensioned in relation to the needle in order to provide a blood flow passage therebetween. A second flashback chamber is formed in the inserter unit and connected to the needle to receive blood flow. The guide wire serves as a guide for the catheter as the catheter is advanced off of the needle, along the guide wire and into the blood vessel. The guide wire and the catheter are separable after the catheter is placed in the blood vessel.

15 Claims, 7 Drawing Sheets

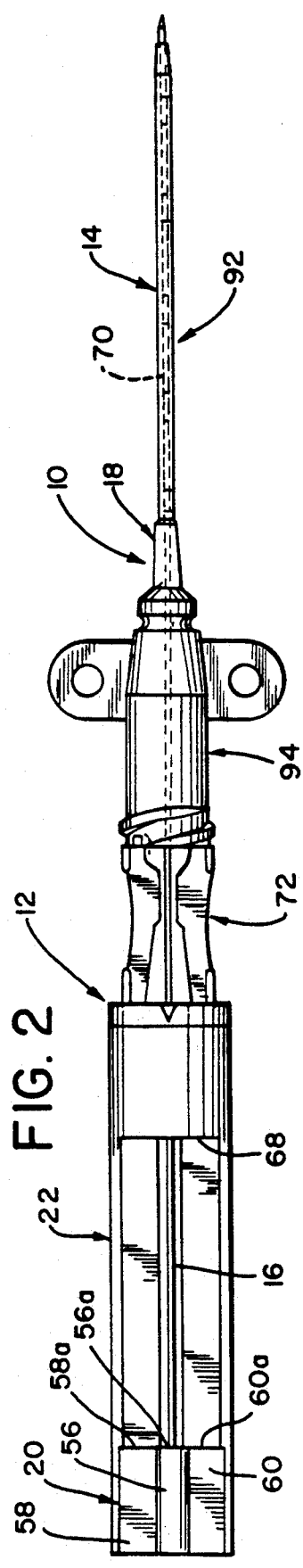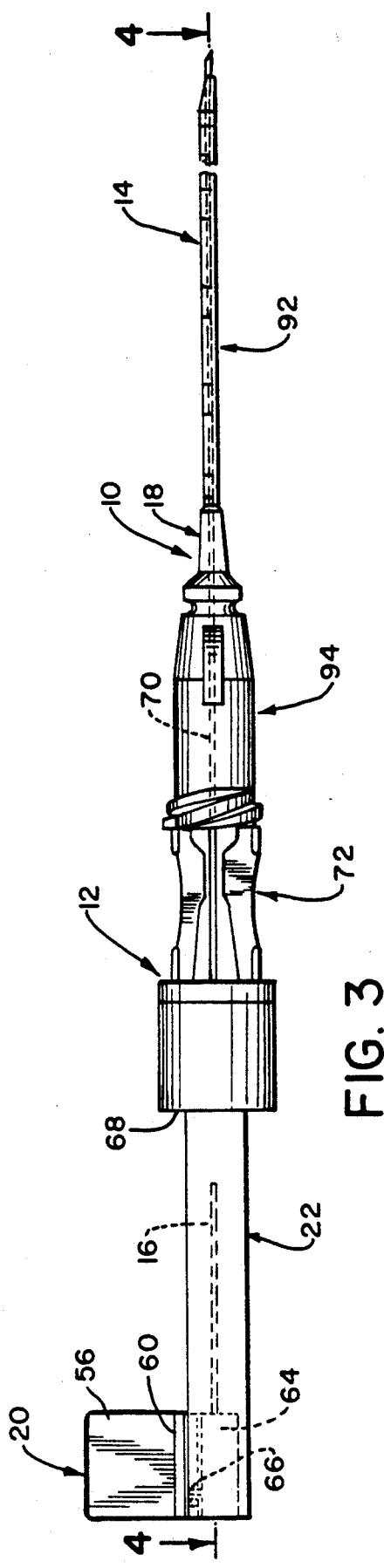

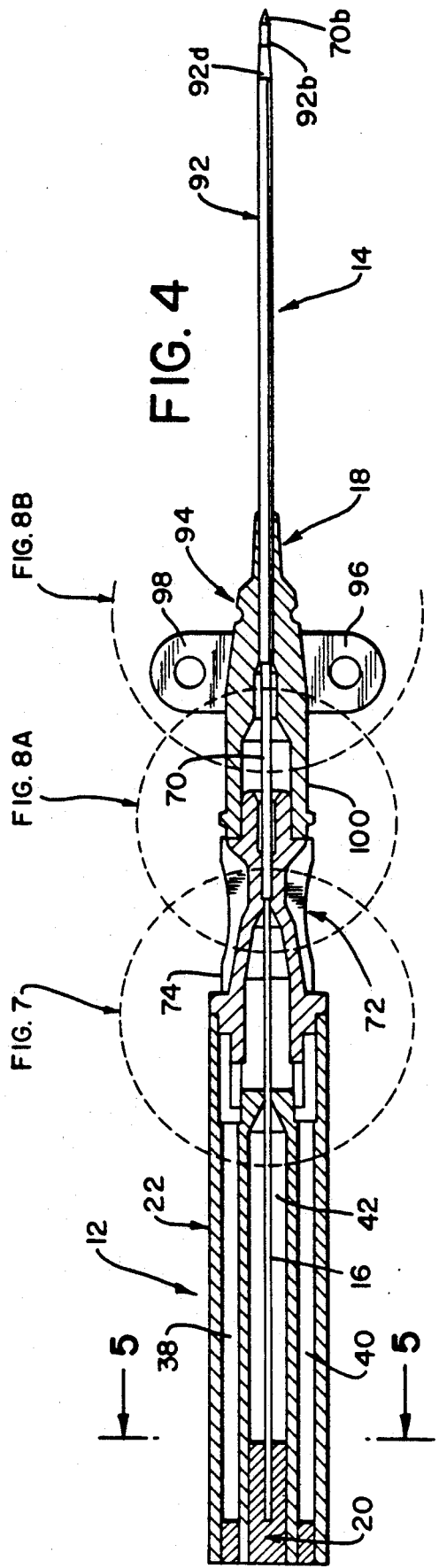
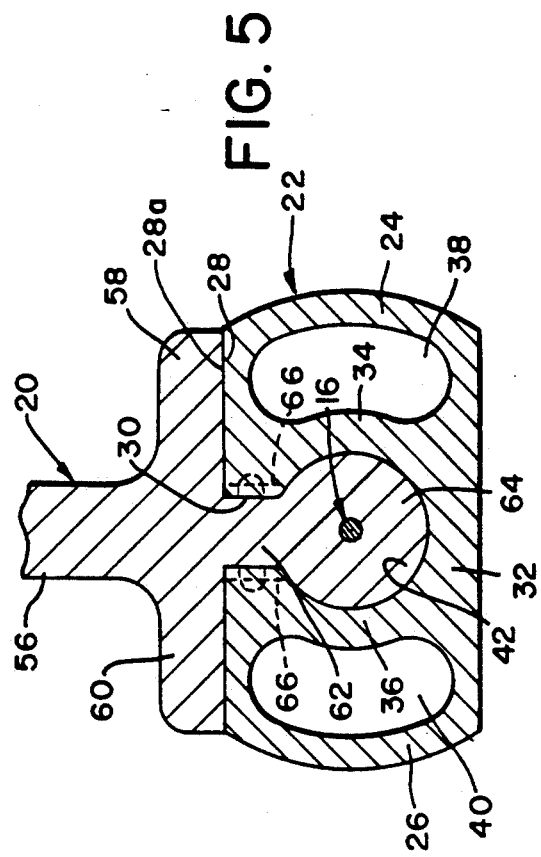

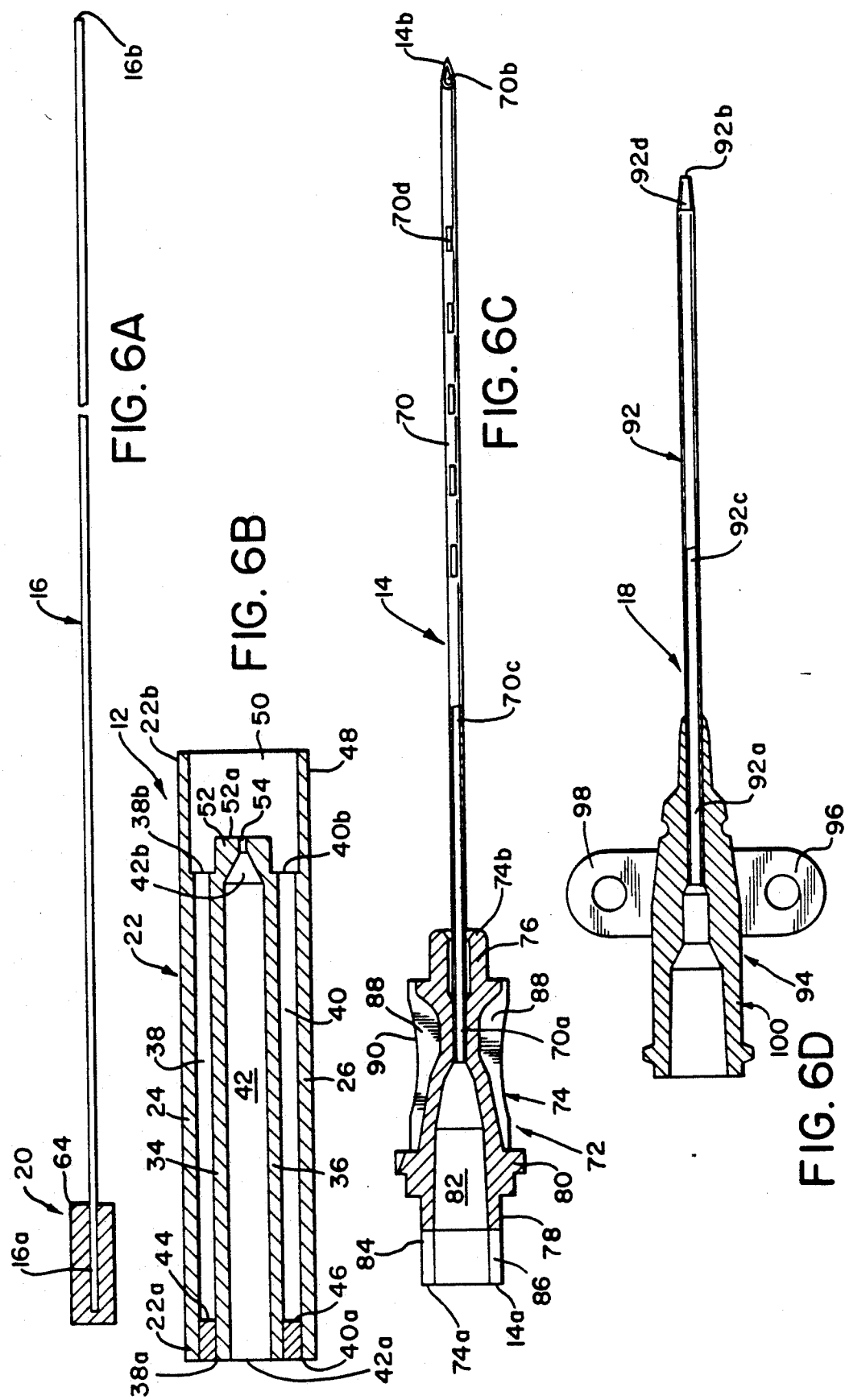

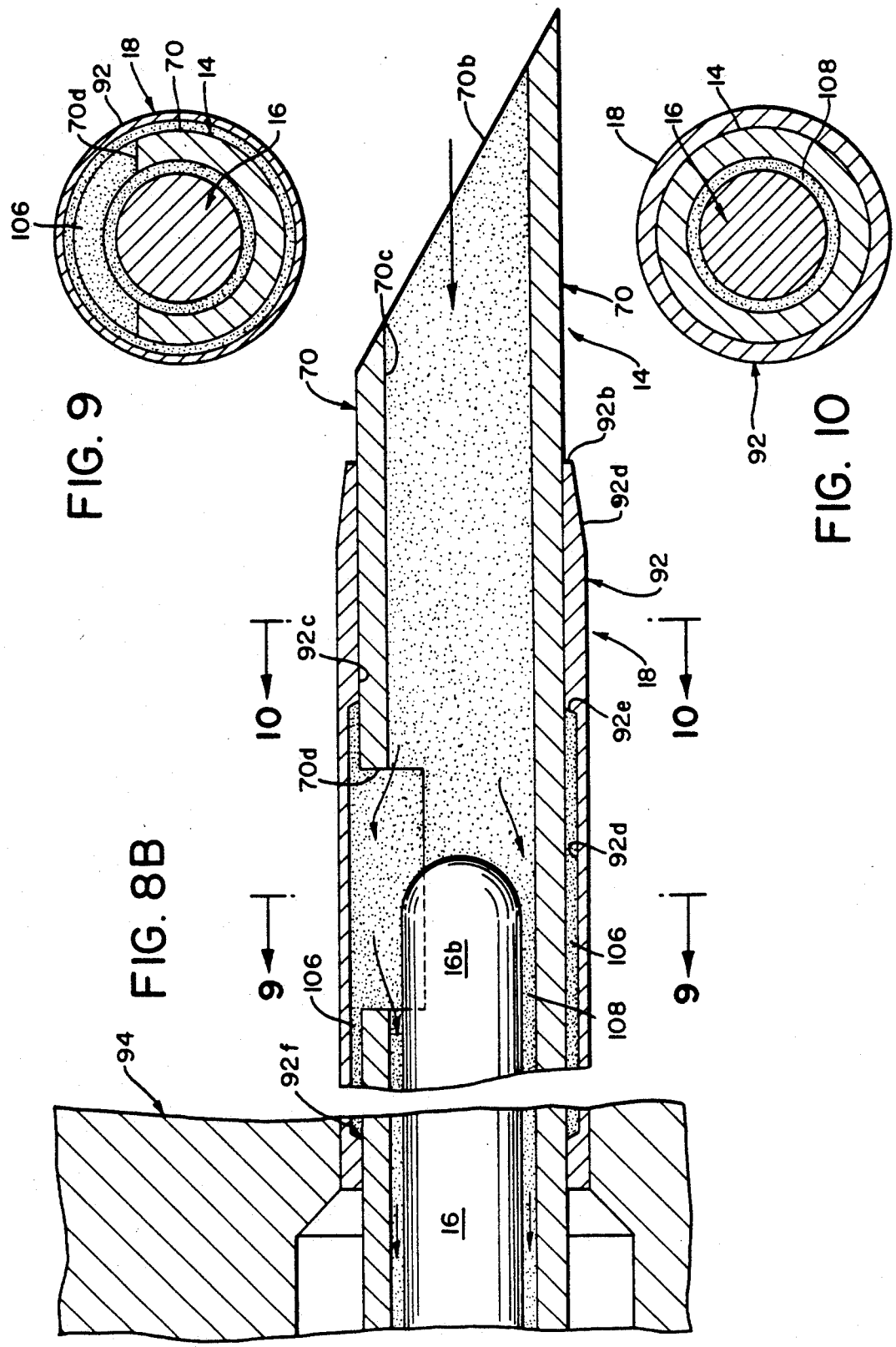

CATHETERIZATION SYSTEM

FIELD OF THE INVENTION

This invention relates to improved catheterization systems and, more particularly, to a compact and bloodless system for introducing an over-the-needle catheter into a blood vessel utilizing a wire guide.

BACKGROUND OF THE INVENTION

Over the years, many systems have been used for introducing a catheter into a blood vessel using a wire to guide the catheter into the vessel. One system involves the use of a hollow introducer needle having an over the needle catheter mounted thereon. After the bevelled tip of the introducer needle is inserted into the blood vessel, as indicated by "flashback" (i.e., the flow of blood from the punctured vessel through the hollow needle and out the proximal end thereof), a wire guide is fed through the hollow introducer needle and advanced until the desired length of the wire guide is within the blood vessel. The catheter is then advanced of of the introducer needle onto the wire guide and into the blood vessel.

Another system is shown in U.S. Pat. No. 4,417,886 entitled "Catheter Introduction Set" ("the '886 Patent"), which discloses a catheter introduction set for the introduction of an over the needle catheter into a relatively small diameter blood vessel. The set includes a hollow needle, an over-the-needle catheter, and a wire guide with the needle and wire guide contained in a single unit. The catheter is carried on the hollow needle and the wire guide is located within the hollow needle. After puncturing the vessel using the needle, blood flashback is visualized in the clear hub of the introducer needle (to provide a positive indication that the needle is actually within the vessel) and the wire guide is then advanced through the hollow needle and into the blood vessel. The over-the-needle catheter is then advanced off of the needle, onto the wire guide and into the vessel, after which the inserter unit (the introducer needle and the wire guide) is removed from the inserted catheter and may be thrown away. The placed catheter is connected to a stop cock, injection cap or to an appropriate connecting tubing. Although the set described in the '886 Patent has enjoyed success, aspects thereof require improvement, particularly with respect to the size of the system, the desirability of instantaneously visualizing flashback and the ever increasing requirement of developing patient care systems which minimize contact by healthcare workers with patient fluids including, principally, blood.

A catheterization system which exhibits some of the advantages of the '886 Patent is shown in U.S. Pat. No. 4,894,052 of Jan. 16, 1990 entitled "Flash Detection In An Over-The-Needle Catheter With A Restricted Needle Bore" ("the '052 Patent"). In the '052 Patent, a translucent over-the-needle catheter is mounted over an introducer needle having a bevelled tip. The distal end of the catheter is provided with a tight fit with the distal end of the needle, while the inside diameter of the catheter is dimensioned in relation to the outside diameter of the needle to provide an annular flashback chamber therebetween, which chamber is closed at its distal end and open at its proximal end.

The hollow needle is connected to the annular flashback chamber by an access port formed in the needle near the distal tip of the catheter such that, upon penetration of the vessel by the needle, there will be rapid visualization of flashback of blood into the annular flashback chamber. To facilitate the insertion of the catheter into the vessel, a guide wire is positioned within the hollow needle. After flashback blood enters the annular flashback chamber via the access port, the wire guide is advanced into the vessel and the over the needle catheter is then moved off the needle and along the guide wire into the blood vessel. Advancement of the wire guide into the vessel serves to obstruct the access port, thereby limiting the free flow of flashback blood into the annular chamber.

Upon placement of the catheter in the vessel, the inserter unit, which includes the syringe, the introducer needle and the guide wire, is separated from the placed catheter a which point the catheter may be appropriately connected for its intended purpose. Although early flashback can be visualized in this prior art system, there are a number of disadvantages including overall size, the need to use a construction much like a hypodermic syringe with its complexities, etc.

Still other prior art systems are available for inserting catheters utilizing wire guide techniques and providing for flashback visualization to permit confirmation of the proper placement of the introducer needle into the blood vessel. One such system is identified as the Arrow EID Catheter which includes a self-contained J spring wire guide which is inserted through a thin wall introducer needle to assist advancement and accurate placement of the catheter in any central vein. In this system, flashback is visualized by the flow of flashback blood through the introducer needle and about the J shaped spring wire guide to an aspiration syringe. In the Arrow EID Catheter, the wire guide is initially in its retracted position. The vessel is punctured by the introducer needle, and blood flashback indicates successful entry into the vein. After stabilization of the introducer needle, the spring wire guide is advanced as required into the vessel and the catheter is moved forward along the spring wire into the vessel.

A significant problem with many prior art designs is that they are not bloodless. For example, some flashback chambers are designed so that blood within the chamber leaks out and may then come in contact with nurses and physicians. Other designs permit blood leakage through the wire guide insertion assembly. Still other designs permit leakage at the needle hub. As can be readily ascertained by inspection of the prior art systems, there remains a need for a compact, bloodless catheterization system which provides an early visual indication of flashback, is readily mass produced, easily packaged and sterilized and convenient for use preferably in a one hand operation. In such design, it would be highly desirable for the user to be able to see the flashback as soon as it enters the introducer needle to provide a prompt indication of the proper placement of the introducer needle into the vessel as the first step in the placement of the over-the-needle catheter into the vessel with the aid of a wire guide.

SUMMARY OF THE INVENTION

This invention is directed to a system for introducing an over-the-needle catheter into a blood vessel, the system includes a body and a hollow needle having a proximal end connected to the body. The needle is also formed with a distal needle tip and at least one port close to the needle tip. A catheter having a lumen terminating at a distal catheter tip is adapted to be carried on the needle and is dimensioned in relation to the needle such that upon placement of the catheter over the needle, the catheter and the needle cooperate to form a first flashback chamber therebetween. The first chamber is in communication with the interior of the hollow needle, and the catheter is at least partially translucent to enable the visualization of blood flow into the first chamber upon insertion of the needle tip into a blood vessel. A guide wire having a distal end is slidably mounted in the body and within the hollow needle, and dimensioned in relation to the needle to provide a blood flow passage therebetween. The guide wire is movable between a first position in which its distal end is wholly within the hollow needle, and a second position in which the distal end extends beyond the needle tip. A second flashback chamber is formed in the body and connected to the needle to receive blood flow upon insertion of the needle tip into a blood vessel.

BRIEF DESCRIPTION OF THE DRAWINGS

Other objects, features and advantages of the present invention will be understood from the following detailed description of a preferred embodiment of the present invention, when taken in conjunction with the accompanying drawings wherein:

FIG. 2 is a top view of the catheterization system showing the inserter unit and the catheter mounted thereon;

FIG. 3 is a side view of the catheterization system shown in FIG. 2 showing the introducer needle in the bevel up position and with the guide wire actuating lever in its fully retracted position at the proximal end of the inserter unit;

FIG. 4 is a partial sectional view taken along the lines 4—4 of FIG. 3 and showing details of the internal construction of the inserter unit including the guide wire and its actuator which are shown in the retracted position;

FIG. 5 is an enlarged sectional view taken along the lines 5—5 of FIG. 4 and showing the proximal end of the inserter unit including the actuator for the wire guide, the detent mechanisms for retaining the wire guide actuator in the retracted position and the flashback chambers;

FIGS. 6A-6D is a series of partial sectional views showing, from top to bottom, the wire guide (FIG. 6A), the body of the inserter unit (FIG. 6B), the introducer needle assembly showing the multiple blood flashback ports in the needle body (FIG. 6C), and the catheter assembly including the catheter body and catheter hub (FIG. 6D);

FIG. 8B is an enlarged section of the area circled in FIG. 4 (and to the right of the enlargement shown in FIG. 8A) showing the details of the relationship between the introducer needle, the catheter and the wire guide at the distal ends thereof and illustrating, in particular, the flow of blood by stippling from the bevelled needle tip through the bore of the needle and through a needle flashback port into the annular flashback chamber formed between the interior of the catheter and the exterior of the needle;

FIG. 9 is a sectional view taken along the lines 9—9 of FIG. 8B and showing the relationship between the concentric guide wire, needle and catheter and showing the shape of the flashback port in the needle and the overall annular shape of the annular flashback chamber; and FIG. 10 is a sectional view taken along the line 10—10 of FIG. 8B at the location where the lumen of the catheter makes physical contact with the outer diameter of the needle to preclude leakage of blood from the distal end of the annular flashback chamber.

DESCRIPTION OF THE PREFERRED EMBODIMENTS

Figure 1:
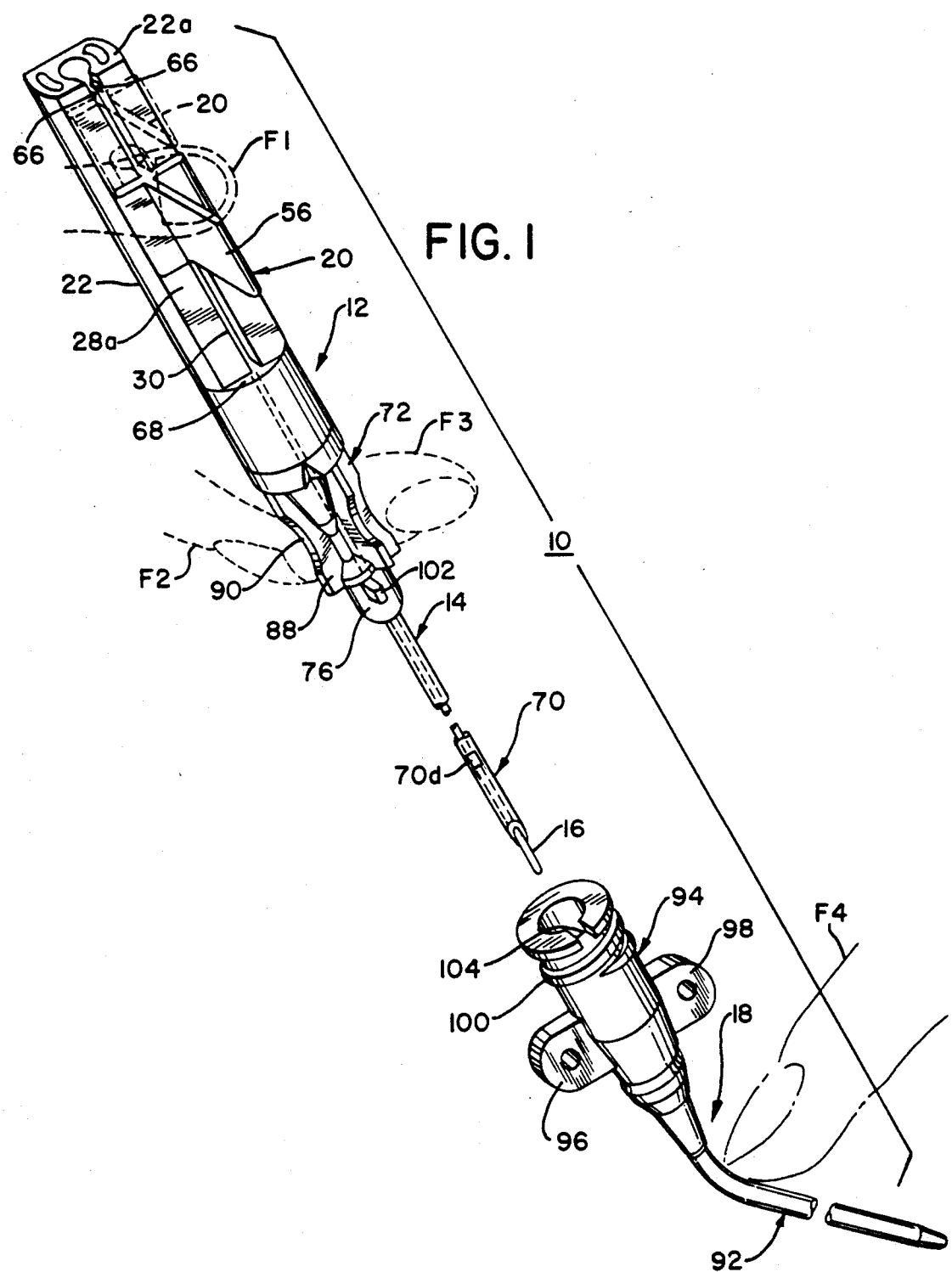
FIG. 1 is an enlarged, exploded perspective view of a preferred embodiment of the catheterization system of the present invention with the catheter being separated from the inserter unit and with the catheter shown being pinched off to prevent blood flow through the catheter (e.g., after placement in the blood vessel) and with typical finger positions shown on the inserter unit for one handed manipulation thereof.

FIG. 1 shows the catheterization system 10 with its two major components (the inserter unit 12 and catheter assembly 18) separated from one another for purposes of illustration. The inserter unit 12 (which is preferably disposable after use) is made up of a needle assembly 14, a guide wire 16 having an actuator 20 connected to the proximal end thereof and a body 22. The needle assembly 14 is connected to the body 22, which body 22 also carries the actuator 20 of the guide wire 16. The actuator 20 is movable along the length of the body 22 to advance the guide wire 16 from its normal retracted position to an extended position as described in detail hereinbelow. The actuating lever 20 is located such that it may be manipulated by the thumb F1 of the person placing the catheter while the inserter unit 12 is grasped between the forefinger F2 and index finger F3 thereby facilitating one handed operation of the system 10. Further, there is illustrated a finger F4 placed on the flexible portion of the catheter assembly 18 for the purposes of pinching off blood flow (after the catheter assembly 18 has been inserted into a vessel) to enable attachment of an appropriate stop cock or the like.

Figure 8A:
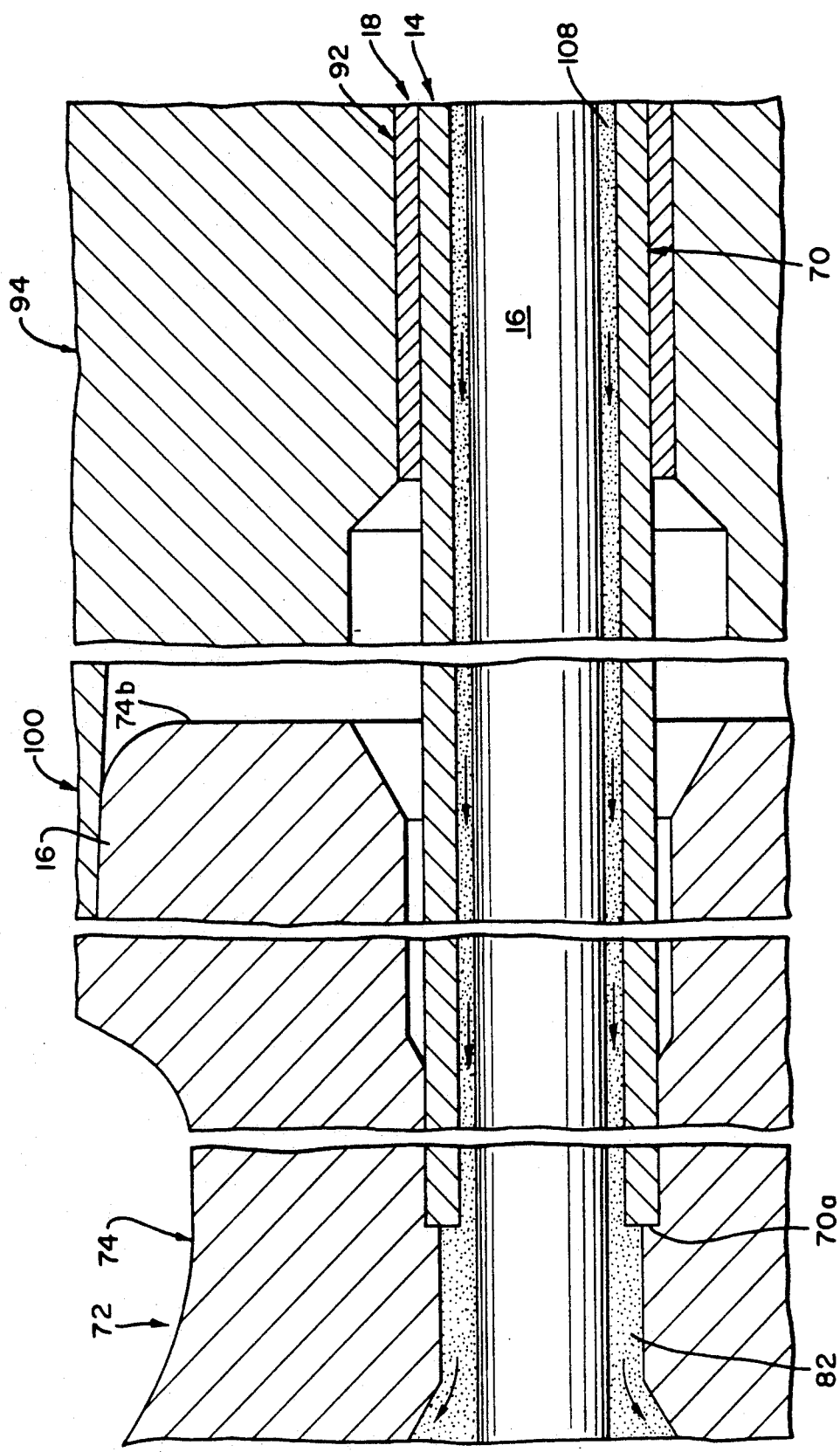
FIG. 8A is an enlarged section of the area circled in FIG. 4 (and to the right of the enlargement shown in FIG. 7) showing the releasable connection between the needle hub of the inserter unit and the catheter hub.

Prior to use, the catheterization system 10 is in the assembled position shown in FIGS. 2-4, inclusive, in which the inserter unit 12 removably carries the catheter assembly 18 on the needle assembly 14 in an over the needle position. FIGS. 2-4 show the actuator 20 in its normal retracted position at the proximal end of the inserter unit 12. In this retracted position, the distal end of the guide wire 16 is located within the needle assembly 14 as shown in FIG. 8B. The needle assembly 14 is of a length in relation to the catheter assembly 18 such that when the catheter assembly 18 is on the needle assembly 14 the distal end of the needle assembly 14 (shown to the right in FIGS. 2-4 & 8B) extends beyond the distal end of the catheter assembly 18.

The catheterization system 10 is constructed from four basic parts which are separately shown in FIGS. 6A-6D prior to assembly of the system 10. FIG. 6A shows the guide wire 16 and its actuator 20. The proximal end 16a of the guide wire 16 is physically attached to the actuator 20 while the distal end 16b is formed with a rounded (e.g., semi spherical) tip (See FIG. 8B). FIG. 6B shows the body 22 of the inserter unit 12 which body receives the guide wire 16 and slidably carries its actuator 20. Body 22 is connected to the needle assembly 14, as shown in FIG. 6C. The needle assembly 14, in turn, carries the over the needle catheter assembly 18 shown in FIG. 6D.

The body 22, shown in the enlarged cross section of FIG. 5, includes spaced side walls 24, 26 which, for convenience and ease of handling are slightly rounded or outwardly bowed (see FIGS. 1 and 5), an interconnecting top wall 28 which has a medial and longitudinally extending slot 30 and an interconnecting bottom wall 32. Additionally, the body 22 is formed with internal dividing walls 34, 36 which are appropriately shaped to form two spaced channels 38, 40 which constitute the second or main flashback chamber located within the unit body 22. Specifically, the walls 24, 34 and the contiguous portions of the walls 28, 32 form the elongated channel 38 extending along side wall 24 and visible therethrough, with the channel 40 being similarly formed and likewise being visible through its contiguous external wall 26. Centrally of the body 22, divider walls 34, 36 are shaped along with the top and bottom walls 28, 32 to provide a longitudinally extending medial track 42 which, as seen in FIG. 5, is open through top wall 28 of the body 22 through slot 30 which is substantially coextensive with the track 42.

Referring to FIG. 6B, the body 22 has a proximal end 22a and a distal end 22b. Opening through the proximal end 22a of the unit body 22 are the spaced open proximal ends of the channels 38, 40 designated respectively as 38a, 40a; and the proximal open end 42a of the track 42. The proximal ends 38a, 40a of the channels 38, 40 are closed against blood flow by porous plugs 44, 46 which enable the purging of air. At their distal ends 38b, 40b, the channels 38, 40 communicate with the internal cavity 50, created by the projecting wall 48. Internal cavity 50 receives the proximal end of the needle assembly 14, as will be subsequently described, to complete paths from the distal tip 14b of the needle assembly 14 to the proximal ends 38b, 40b of the channels 38, 40.

Disposed between the distal ends 38b, 40b of the channels 38, 40 and closing off the distal end 42b of the track 42 is a transverse partition 52 which is formed with a guide wire receiving opening 54 through which the guide wire 16 is passed for longitudinal movement relative to the inserter unit 12. The fit between the guide wire 16, which has uniform diameter, and the opening 54 is such as not to interfere with easy sliding movement thereof but, at the same time, to preclude the flow of blood therethrough and into the track 4 (see FIG. 7). As best shown in FIGS. 1 and 6B, track 42 is open at its proximal end 42a and along its top as a result of the provision of the longitudinally extending and medially disposed slot 30 in the top wall 28 of the body 22. The distal or foremost circular face 52a of the partition 52 will, as will subsequently be described, divert the flow of flashback blood into the contiguous distal ends 38b, 40b of the channels 38, 40.

Referring next to FIGS. 1-6 and, in particular, to FIG. 5, there is illustrated the construction of the guide wire actuator 20 which is used for moving the guide wire 16 within the track 42 through a relatively short stroke (e.g. the length of the track 42). Such movement of the actuator 20 results in the projection of the spherical distal tip 16b of the guide wire 16 beyond the distal tip 14b of the needle assembly 14 and into the blood vessel so that the guide wire 16 can perform its guiding function. The guide wire actuator 20 includes an upstanding actuating lever 56 which projects above the top wall 28 of the body 22 and is in a position which is readily accessible to the user (see FIG. 1). The guide wire actuator 20 includes laterally extending stabilizing feet 58, 60 which ride along the flat upper surface 28a of the top wall 28 of the body 22. Projecting downwardly from the stabilizing feet 58, 60 is a connecting web 62 which, in turn, carries a cylindrical slide member 64 which is attached to the proximal end 16a of the guide wire 16 for advancing and retracting the guide wire 16 as a result of the movement of the actuator 20 between limit positions.

Initially, the actuator 20 is disposed in a fully retracted position shown in FIGS. 2 and 3 and contiguous to the proximal end 22a of the body 22. The actuator 20 is releasably held in this retracted position by an appropriate detent mechanism 66 located on the connecting web 62 of the actuator 20 and on the upstanding walls of the slot 30. The detent mechanism 66 may take a variety of forms and here includes outwardly extending projections formed on the opposite upstanding walls of the connecting web 62 which are respectively located between paired positioning projections formed on the upstanding walls of the slot 30 contiguous to the proximal end 22a of the body 22. The projections coact with each other to hold the actuator 20 in the retracted position at the proximal end 22a of the inserter unit 12. In this position, the rounded distal tip 16b of the guide wire 16 is proximal of the distal tip 14b of the needle assembly 14 and optimally in a clearance position with respect to the most distal port 70d (see FIG. 8B), so as not to inhibit the proper functioning of the system, particularly with respect to early visualization of flashback.

Upon movement of the actuator 20 from its initial retracted position toward its extended position, i.e, toward the distal end 22a of the body 22, the leading edge of the upstanding actuating lever 56 and the leading edges of the stabilizing feet 58, 60 will contact an upstanding abutment 68 located on the body 22 (See FIG. 1). Such contact limits the movement of the actuator 20 and the corresponding amount of extension of the distal tip 16b of the guide wire 16 past the distal tip 14b of the needle assembly 14 and into the blood vessel. The entire sub-assembly of the actuator 20 and the guide wire 16 may be withdrawn (against the minimal resistance of the detent mechanism 66) from the proximal end 42a of the guideway 42 so that the guide wire 16 and actuator 20 may be separated from the system 10 for use independently of the system.

Reference will now be made to FIG. 6 in conjunction with FIGS. 4 and 7 for an explanation of the needle assembly 14 and the manner in which it is connected to the body 22.

The needle assembly 14 includes an elongated needle body 70 of an appropriate gauge typically in the range of 16-24. The needle body 70 is mounted at its proximal end 70a on the needle hub 72 and is formed with a bevelled distal tip 70b. The needle body 70 includes a needle bore 70c of uniform cross-section which receives, with appropriate clearance and as will subsequently be described, the wire guide 16. The operative orientation of the needle body 70 is with the bevel 70b up. Also along the uppermost surface of the needle body 70, there are provided a series of flashback blood ports 70d arranged in spaced relation with each other along a length of the needle body 70. The blood ports 70d, along with the catheter assembly 18, provide a first flashback chamber. Specifically, the ports 70d in the needle body 70 are spaced proximally of the bevelled tip 70b to provide an intermediate section of the needle body 70 which will cooperate with the catheter 18 to provide an early or first flashback chamber, located between the outside wall of the needle body 70 and inside wall of the catheter assembly 18. The spacing of the most distal port 70d is such that only a relatively short path for blood flow exists from the bevelled distal tip 70b of the needle body 70 through the needle bore 70c and into such first of the series of flashback ports 70d.

The needle hub 72 includes a hub body 74 having a proximal end 74a and a distal and 74b. At its distal end 74b the needle body 74 is formed with a male luer slip or cylindrical supporting plug 76 which is sized for releasable but fluid tight (but not air tight) connection to a female luer lock connector or hub, to be described, on the proximal end of the catheter assembly 18. Contiguous to its proximal end 74a, the hub body 74 is formed with a male needle mounting hub 78 which is sized to be received within the projecting cylindrical wall 48 of the body 22. The hub body 74 includes a step 80 which is sized to fit into and close off the cavity 5 in the distal end 22b of the body 22, as seen best in FIGS. 4 and 7.

Figure 7:
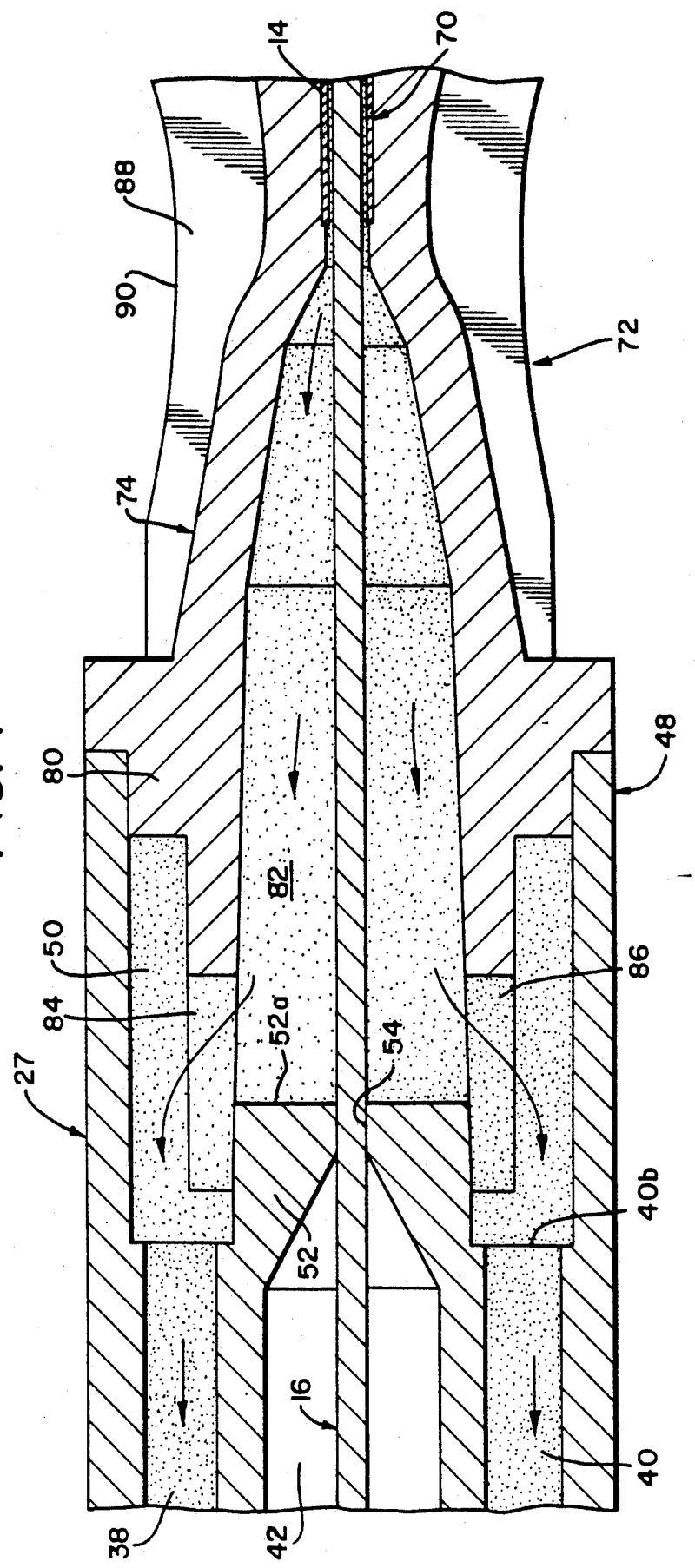
FIG. 7 is an enlarged section of the area circled in FIG. 4 showing details of the permanent connection between the needle hub and the body of the inserter unit and illustrating, by stippling, the blood flow paths from the cavity of the needle hub to the two separate main flashback chambers.

Referring now to FIGS. 6B, 6C and 7, the hub body 74 is provided with an internal cavity 82 which, at its distal end, communicates with the needle bore 70c and, at its proximal end, is formed with ports 84, 86 which establish lateral openings at either side of the partition 52 of the body 22 such that the flashback blood diverted by the surface 52a may flow into the adjacent distal ends 38b, 40b of the channels 38, 40 (See FIG. 7). In-between the step 80 and the male luer slip 76, the needle hub body 74 is formed with four radially extending finger pieces 88 at 90° circumferential spacings which are appropriately contoured at their outermost edges to provide gripping or finger receiving notches or depressions 90 (see, in particular, FIG. 1) When the hub 72 of the needle assembly 14 is mounted on the distal end of the body 22 and permanently attached thereto for example by use of an appropriate adhesive or by sonic welding or the like, it will be seen that a continuous path for flashback blood is established from the bevelled tip 70b of the needle body 70 through needle hub cavity 82 and via the ports or windows 84, 86 into the channels 38, 40 formed in the body 22.

As best shown in FIG. 6, the catheter assembly 18 is seen to include an elongated catheter body 92 having proximal and distal ends 92a, 92b and an internal lumen or bore 92c. The end of the catheter body 92 contiguous to the distal tip 92b is formed with a progressively decreasing cross section or tapered tip to facilitate insertion into the blood vessel. The catheter body 92 is supported at its proximal end by a catheter hub 94 which is illustrated as having laterally projecting suture wings 96, 98, although it is understood that the catheter hub 94 may be provided with other means (or no means) for the retention of the catheter assembly 18 on the patient after placement. The catheter hub 94 is formed with an integral female luer lock or connector 100. In order to orient the catheter 18 in relation to the inserter unit 12 when the male slip 76 of the needle assembly 14 is inserted into female luer lock 100, the proximal end of the hub body 74 is formed with an orienting key or lug 102 (see FIG. 1) which is received within an appropriately oriented keyway or orienting notch 104 formed in the proximal end of the luer lock or connector 100.

As to the selection of materials for the manufacture of the several components of the catheterization system 10, it will be understood that the disposable inserter unit 12 must be fabricated, at least as to those walls which will provide visualization of the content of the channels 38, 40, of a transparent material, typically of a moldable thermoplastic material having the requisite properties to withstand sterilization. The needle body 70 is formed of an appropriate metal, typically 304 S.S., such that the port 70d, provided for visualization of flashback blood, as will be described, may be ground into the upper surface of the needle body 70. The guide wire 16 may be fabricated of metal, plastic, or a combination thereof and is constructed to provide its spherical or rounded soft distal tip 16b. Finally, the catheter body 92 includes at least some clear or translucent elongated circumferentially extending sections and may be fabricated from a striped single lumen catheter blank which includes circumferentially extending sectors of clear polyurethane separated by longitudinally extending circumferential filler sections of a radiopaque polyurethane. Any appropriate technique may be utilized for the manufacture of the catheter body or blank to enable visualization of flashback blood in the first or early visualization flashback chamber, as will now be described.

Reference will now be made to FIGS. 8A, 8B, 9 and 10 for a description of closed ended annular first or early visualization flashback chamber, generally designated by the reference numeral 106 formed between the catheter body 92 and the needle body 70 when the catheter assembly 18 is carried on the needle assembly 14 in the over the needle position. Specifically, the interior of the catheter body 92 is provided with a relatively shallow longitudinally extending well 92d having its distal portion 92e located distally of the first flashback port 70d and its proximal end 92f located proximally of the last of the flashback ports 70d formed in the uppermost surface of the needle body 70. Between the distal end 92e of the well 92d and the distal end 92b of the catheter body 92, there is a relatively snug fit between the interior wall of the catheter body 90 and the exterior wall of the needle body 70. Thus, in the initial over the needle position of the catheter assembly 18 on the needle assembly 14, there will be no leakage between the distal end 92e of the first flashback chamber 106 and the distal end of the needle assembly 14 when blood flows from a vessel through the needle bore 70c and into the first flashback chamber 106 through ports 70d. Comparably, at the proximal end 92f of the shallow well or recess 92d, there is a comparable snug fit between the catheter body 92 and the needle body 70 (see the right side of FIG. 8A and the left side of FIG. 8B) to close off the proximal end of the annular flashback chamber 106 to prevent any leakage of blood. However, air may escape into the atmosphere through the proximal end of the annular flashback chamber 106 and between the male slip 76 of the needle assembly 14 and the female luer lock 100 of the catheter assembly 18 in order to permit blood flow into the flashback chamber 106.

As seen best in FIG. 8B, when the wire guide 16 is in the retracted position its spherical distal tip 16b is disposed in a non-obstructing or clearance position in relation to the most distal or first blood flashback port 70d encountered by the initial blood flow from the needle bore 70c. Various non-obstructing positions can be established for the wire guide 16 in relation to the first flashback port 70d. In this particular illustrative embodiment, the distal tip 16b of the wire guide 16 is shown substantially intermediate the distal and proximal ends of the first flashback port 70d which is adequate to provide an unobstructed blood path to the first flashback port 70d, with the spherical tip 16b serving as a diverter of the blood flow. The specific orientation of the distal tip 16b of the wire guide 16 relative to the needle assembly 14 represents a design compromise. The design objective is to provide a compact and foreshortened system, which requires that the distal tip 16b of the wire guide 16 be as close as practical to the distal end 14b of the needle assembly 14 without interfering with entry of blood into the first flashback chamber 106.

Flashback visualization will occur throughout the length of the first flashback chamber 106 due to the provision of the multiple flashback ports 70d (see FIG. 6). The diameter of the wire guide 16 is selected in relation to the diameter of the needle bore 70c to provide an annular blood flow passage 108 therebetween which communicates with the first flashback chamber 106 through the spaced ports 70d. Thus, when the wire guide 16 is in the retracted position as shown in FIG. 8B, two flow paths are established for flashback blood, namely, a first path through the multiple flashback ports 70d and into the first flashback chamber 106 and a second path via the annular blood flow passage 108 extending along the longitudinal extent of the wire guide 16 from its distal tip 16b, into the cavity 82 of the hub body 72, through the lateral ports or windows 84, 86, into the cavity 50 formed at the distal end 22b of the body 22, and thence into the distal ends 38b, 40b of the channels 38, 40 of the second flashback chamber.

During a typical manufacturing sequence, the disposable inserter unit 12 is initially assembled by connecting the needle assembly 14 to the body 22, with the step 80 of the needle hub 72 closing off the distal end 22b of the body 22 and with the male needle mounting hub 76 received within the projecting cylindrical wall 48 of the body 22. The guide wire 16 and its actuator 20 is then assembled on the body 22. The guide wire 16 is threaded through the partition opening 54 aided by the funnel formed at the distal end 42b of the track 42. The guide wire 16 is then advanced through the cavity 82 and into the needle bore 70c until the distal tip 16b of the guide wire 16 is spaced proximally of the tip 14b of the needle assembly 14 in its flow diverting position in relation to the first of the ports 70d in the needle body 70 (see FIG. 8B).

Upon placement of the catheter assembly 18 into its over-the-needle position (see, for example, FIGS. 2, 3, 4), the well 92d formed in the interior of the catheter body 92 cooperates with the needle body 70 to form the first flashback chamber 106. Orientation of the catheter assembly 18 in relation to the needle assembly 14 is accomplished by the key 102 entering the orienting notch 104; and, in this position, the distal catheter tip 92b is disposed proximal to the distal needle tip 70b and in the appropriate position in relation to the several ports to form the first flashback chamber 106. Of course when the guide wire 16 is in its retracted position the actuator 20 is at the proximal end 22a of the body 22 and is held in this position for packaging, sterilization and shipment by the detent mechanism 66 (see FIG. 1 in which the actuator 20 is in a dotted line position slightly forward of the proper retracted position to generally show the detent mechanism 66).

In a typical sequence of use for a catheterization procedure, the user prepares the puncture site in the usual manner and then peels open the sterilized and sealed package to remove the system 10. Typically, the system 10 is sold with a protective shield (not shown) disposed over the catheter body 92 and the projecting distal tip of the needle assembly 14 and this protective shield is removed. By grasping and manipulating the actuating lever 20, the user may try out the advancement and retracting of the spring wire guide 16 through the needle assembly 14 to ensure proper feeding. Additionally, the user may make the election of whether or not to utilize the suture wings 96, 98 since, typically, the suture wings can be removed from the catheter hub 94 such that the user may use a different procedure for securing the catheter assembly 18 to the skin of the patient after placement. After testing and taking these preliminary steps, the actuating lever 20 is moved to its fully retracted position at the proximal end 22a of the body 22 to properly position the distal tip 16b of the guide wire 16 as shown in FIG. 8B.

Thereupon, the user punctures the blood vessel with the needle assembly 14 using a continuous, controlled and slow forward movement, exercising caution to avoid transfixing both vessel walls. Successful entry into the blood vessel will be immediately visualized by the appearance of flashback blood initially in the first or early visualization flashback chamber 106 and then in the channels 38, 40 forming the second flashback chamber in the body 22. The user must take care not to inadvertently puncture both vessel walls incident to the introduction of the needle assembly 14 into the blood vessel since this, in turn, could result in the inadvertent sub arterial placement of the wire guide 16.

After stabilizing the position of the needle assembly 14 and careful advancement of the wire guide 16 via the actuating lever 2 (moving through its relatively short forward stroke), the guide wire 16 will be located within the blood vessel for a length predetermined by the permitted stroke of the actuator lever 20. If resistance is encountered while advancing the wire guide 16, the user should not force such feed and should not retract the wire guide 16 while in the blood vessel since this could inadvertently damage the wire guide 16. Rather, the entire system 10 should be withdrawn from the vessel and a new puncture attempted.

After the wire guide 16 is positioned, the user firmly grips the body 22 or the needle hub 72 (e.g., at the depressions 90) and then advances the catheter assembly 18 forwardly along and off the needle assembly 14. The distal end 92b of the catheter assembly 18 tracks the wire guide 16 into the vessel. If difficulty is encountered during catheter advancement, a slight rotation of the catheter hub 94 might be helpful. Thereupon, the user holds the catheter 18 in place and removes the inserter unit 12, at which point the physician attaches the desired stopcock, injection cap or connecting tube to the luer connector 100 of the catheter hub 94. The final step is to secure the catheter to the patient in a preferred method, for example, by using the wings 96, 98 and to cover the puncture site with a suitable dressing.

From the foregoing, it will be appreciated that there has been provided an exceptionally compact, bloodless design for placement of catheters into blood vessels which enables the user to readily master a simple insertion technique, thereby increasing the percentage of successful first-time placement. Flashback blood is effectively contained within the disposable inserter unit 12 and unobstructed blood flow can be stopped prior to separation of the disposable inserter unit 12 from the displaced catheter assembly 18 by appropriately depressing the catheter body 92 to effectively close the catheter lumen. On those occasions when it is desirable for the physician to have direct access to the guide wire 16 and its actuator 20 this sub-assembly may be readily removed from its operative and mounted position on the body 22 of the inserter unit 12.

Although the invention has been described with reference to particular embodiments, it is understood that these embodiments are merely illustrative of the different aspects and features of the invention. A person skilled in this art may make numerous modifications to the illustrative embodiments described herein and other arrangements may be devised to implement the essential features of the present invention without departing from the spirit and scope of the invention as described and claimed herein.

What we claim is:

1. A system for introducing an over the needle catheter into a blood vessel comprising
   a body,
   a hollow needle body having a proximal end connected to said body and formed with a distal needle tip and at least one port close to said needle tip,
   a catheter body having a lumen terminating at a distal catheter tip, said catheter body adapted to be carried on said needle body and being dimensioned in relation to said needle body such that upon placement of said catheter body over said needle body said catheter body and said needle body cooperate to form a first flashback chamber therebetween, said first chamber being in communication with the interior of said needle body through said port, and said catheter body being at least partially translucent to enable the visualization of blood flow into said first chamber upon insertion of said needle tip into a blood vessel,
   a guide wire having a distal end, said guide wire slidably mounted in said body and within said needle body and dimensioned in relation to said needle body to provide a blood flow passage therebetween, said guide wire being movable between a first position in which its distal end is wholly within said needle body and a second position in which said distal end extends beyond said needle tip,
   a second flashback chamber formed in said body and connected to said needle body to receive blood flow upon insertion of said needle tip into a blood vessel.

2. A system according to claim 1 wherein when said guide wire is in said first position, said distal end is in a clearance position with respect to said port.

3. A system according to claim 1 wherein said second chamber includes venting means to allow air to escape from said second chamber but not blood.

4. A system according to claim 1 wherein said body includes mounting means for slidably receiving said guide wire including a partition having a guide wire opening, said guide wire being disposed through said guide wire opening with a sliding fit which precludes blood flow therethrough.

5. A system according to claim 4 wherein said partition extends in a direction substantially transverse to the path of movement of said guide wire.

6. A system according to claim 5 wherein said partition is arranged to divert the flow of flashback blood from said needle body to said second chamber.

7. A system according to claim 4 wherein said body includes a track formed therein and terminating at one end in said partition, said guide wire having a proximal end extending into said track and connected to an actuator slidably mounted in said track.

8. A system according to claim 7 in which said actuator includes a lever which extends external to said body for moving said guide wire.

9. A system for introducing an over-the-needle catheter into a blood vessel, comprising:
   (A) an inserter unit including a body having a proximal blood flashback chamber,
   (B) a hollow needle body connected to said body and including a distal needle tip and at least one port,
   (C) a catheter body removably carried on said needle body and formed with a lumen terminating at a distal tip,
   said catheter body and said hollow needle body cooperating to form a distal blood flashback chamber when said catheter body is carried on said needle body, and said port permitting blood flow from said needle body into said distal flashback chamber,
   (D) a guide wire having a distal tip, and
   (E) means on said body for mounting said guide wire thereon for movement between a retracted position in which said guide wire distal tip is within said needle body and an extended position in which said guide wire distal tip extends beyond said needle tip to serve as a guide for said catheter body during introduction of said catheter body into a blood vessel, said guide wire being dimensioned in relation to the interior of said needle body to define an annular flashback passage leading from said needle tip through said needle body to said proximal flashback chamber.

10. A system according to claim 9 wherein said means on said body for mounting said guide wire includes a track formed in said body and an actuator slidably mounted in said track and operatively connected to said guide wire.

11. A system according to claim 10 wherein said track has proximal and distal track ends and said body includes a partition closing said distal end of said track, said partition being formed with a partition opening through which said guide wire extends, said partition opening being dimensioned to provide a sliding fit with said guide wire whereby said track is effectively blocked from receiving flashback blood flowing through into said proximal flashback chamber.

12. A system according to claim 11 wherein said proximal track end is opened such that said actuator and guide wire may be removed from said body.

13. A system according to claim 12 including detent means on said body and said actuator for releasably retaining said actuator against movement in said track and retaining said guide wire in said retracted position.

14. A system for introducing an over the needle catheter into a blood vessel comprising
   a needle assembly including a needle body defining a needle bore and terminating at a distal needle tip, said needle body being provided with at least one flashback port contiguous to said needle tip,
   a catheter assembly including a catheter body having a lumen terminating at a distal catheter tip, said catheter body being dimensioned in relation to said needle body such that upon placement of said catheter in an over-the-needle position on said needle, said catheter and said needle cooperate to provide a first flashback chamber which chamber is in communication with said needle bore through said flashback port, said catheter body being at least partially translucent to enable the visualization of blood flow into said first flashback chamber upon insertion of said needle tip into a blood vessel to initiate blood flow into said needle body, a guide wire having a distal end and mounted in said needle bore and dimensioned in relation to said needle body to provide a blood flow passage therebetween, said guide wire having a retracted position in which its distal end is substantially clear of said flashback port and contiguous to said needle tip and an extended position in which said guide wire distal end extends beyond said needle tip, said needle assembly connected to a body and said guide wire slidably mounted in said body, an actuator mounted in said body for movement and operatively connected to said guide wire for moving said guide wire between its retracted position and its extended position, a second flashback chamber located in said body, pathway means in said body for establishing a blood flow path from said needle bore to said second flashback chamber, said body being separable from said catheter assembly after said catheter assembly is placed in a blood vessel.

15. A system according to claim 14 wherein said second flashback chamber includes venting means to vent air from said second flashback chamber to the atmosphere and retain flashback blood in said second flashback chamber.

* * * * *